United States Patent
Ehwald

(10) Patent No.: US 6,210,326 B1
(45) Date of Patent: Apr. 3, 2001

(54) MICROSENSOR FOR DETERMINATION OF GLUCOSE AND OTHER ANALYSIS IN LIQUIDS BASED ON AFFINITY VISCOSIMETRY

(76) Inventor: Rudolf Ehwald, Strelitzer Str. 56, 10115 Berlin (DE)

( * ) Notice: Subject to any disclaimer, the term of this patent is extended or adjusted under 35 U.S.C. 154(b) by 0 days.

(21) Appl. No.: 08/888,734

(22) Filed: Jul. 7, 1997

(51) Int. Cl.$^7$ .................................................. A61D 5/00
(52) U.S. Cl. ....................... 600/365; 600/345; 600/347; D24/186; 128/903
(58) Field of Search ..................................... 600/300, 301, 600/322, 366, 317, 353; 422/68.1, 52; 205/777.5, 781.5, 403; 73/304, 130.4, 19.03, 28.03, 723; 384/550, 571; 436/50; 435/14

(56) References Cited

U.S. PATENT DOCUMENTS

| | | | |
|---|---|---|---|
| 4,832,034 | * 5/1989 | Pizziconi et al. | 600/366 |
| 5,156,972 | * 10/1992 | Issachar | 422/68.1 |
| 5,174,291 | * 12/1992 | Schoonen et al. | 600/322 |
| 5,269,891 | * 12/1993 | Colin | 205/777.5 |
| 5,615,671 | * 4/1997 | Schoonen et al. | 600/322 |

* cited by examiner

Primary Examiner—John P. Lacyk
Assistant Examiner—Michael Astorino
(74) Attorney, Agent, or Firm—Helfgott & Karas, P C.

(57) ABSTRACT

A microsensor for the determination of glucose and other analytes in liquids, based on affinity viscosimetry. The sensor based on affinity viscosimetry with stable working properties can be sufficiently minaturized for implantation in the organism. The sensor has a completely closed liquid conducting system having a dialysis chamber of a dialysis hollow fiber filled with the aqueous polymer system, and a measuring system for electrical signal transduction working in such a way that the sensitive polymer solution and eventually other liquids which are not miscible but hydraulically coupled with the polymer solution, are able to move on a closed path. The measuring system contains a micromotor to induce the liquid movement and a signal transducer sensitive to either pressure, volume or streaming to form signals related unequivocally to viscosity.

12 Claims, 1 Drawing Sheet

SECTION C ... D

SECTION E ... F

MICROSENSOR FOR DETERMINATION OF GLUCOSE AND OTHER ANALYSIS IN LIQUIDS BASED ON AFFINITY VISCOSIMETRY

BACKGROUND OF THE INVENTION

1. Field of the Invention

The present invention relates to a microsensor for determination of glucose and other analytes in liquids based on affinity viscosimetry.

2. Description of the Related Art

Affinity sensors are important for analytics, as there exists a large number of affinity receptors, e.g. antibodies, which are not catalytically active. The technical task to transduce concentration dependent binding of analytes to the suitable receptor into an electrical signal within a microsensor, is an actual one, which is not easy to solve. A promising way for solving this task consists in the inclusion of receptor proteins and polymer affinity ligands in the lumen of a dialysis hollow fiber with a membrane which is permeable to the analyte (schultz, J. S. and Sims, G., 1979: Affinity sensors for individual metabolites, Biotechn. Bioeng. Symp-9, 65–71, Schultz, J. S., 1982, Optical sensor of plasma constituents, U.S. Pat. 4,344,438). The analyte-dependent dissociation of the receptor from the polymer ligand may be made detectable by diffusion of the polymer binding partner between the immobilized binding site and the ligand phase within the fiber lumen (Schultz, J. S., Mansouni, S. and Goldstein, I. J., 1982: Affinity sensor, A new technique for developing implantable sensor for glucose and other metabolites, Diabetes Care, 5,245–253, Knoll, D., Ehwald, K. E., Ehwald, R. Sorge, E., Ballersätdt, R. und Bolleroth, M., 1991: A silicon based microsystem for continuous in vivo glucose monitoring using a new reversible measuring principle) or by Fluorescence quenching (Meadows, D. L. and Schultz J. S., 1988, Fiberoptic bionsensor based on fluorescence energy transfer, Talante 35, 145–150). An interesting and simple alternative to the mentioned techniques is an affinity viscosimetry, measuring the concentration of affinity bonds mechanically in a direct manner. Affinity viscosimetry with dispersions of dextran and Concanavalin A is suitable for glucose determination in the blood sugar range and may be carried out with dialysis hollow fibers. The until now described hollow fiber viscosimeters do not have an electrical signal transducer and are unstable because of nonavoidable volume changes of the sensitive polymer phase (Ballerstädt, R. und Ehwald, R., 1992, Affinit ätssensor, DE-P4203466, Ballerstädt, R., und Ehwald, R, 1994: Suitability of aqueous dispersion of dextran and Concanavalin A for glucose sensing in different variants of the affinity sensor, Biosensors and Bioelectronics, 9, 557–567).

An important field of application of microsensors is the on-line registration of analytes in body fluids, e.g. of glucose in the blood. Affinity viscosimetry is generally suitable for measuring relevant analytes which are known to bind to affinity receptor proteins. A miniaturized implantable affinity viscosimeter combined with a dialysis chamber or hollow fiber would therefore have promising applications. Such viscosimeter is not known.

BRIEF SUMMARY OF THE INVENTION

It is an object of the present invention to produce a reliably working sensor on the base of affinity viscosimetry which can be sufficiently miniaturized by microsystem technology for implantation purposes.

This and other objects of the present invention are attained by a hydraulic coupling of the sensitive polymer system dissolved in water and a measuring signal delivering system to a closed completely liquid-filled conducting system (hollow conductor). The analyte-sensitive polymer solution and eventually one or more other liquids which are not miscible with this polymer solution are mobile on a closed path. The measuring system contains a micromotor for driving the movement of the analyte-sensitive polymer solution and a pressure-, volume- or flow-sensitive unit delivering signals which are unequivocally related to the viscosity of the liquids.

For example, a hollow conductor with solid walls may be tightly connected at both ends with the endings of a hollow fiber which is filled with the sensitive polymer solution. The whole hollow conductor is filled with a liquid which can transduce forces between a pumping micromotor and the sensitive polymer solution within the fiber. Possible micromotors are magnetic particles or liquids in the magnetic field, dielectrically moved solids or liquids. The liquid movement within the hollow conductor is registrated either optically by photosensors at dragged interfaces or solids, or electromechanically by the reaction of the frictional reactive force on the micromotor. The micromotor is a microsystem on the base of silicon technology, for its application in vivo a microelectronic system with integrated transducing elements for energy and signals is opportune.

According to the invention, there exist several variants, enabling or facilitating galvanic uncoupling of the extracorporal monitoring and energy supply form intracorporal viscosimetric sensing device. For efficient transduction of energy and information it is especially lucrative that apart from the dialysis fiber or chamber, the hollow conductor is filled by a liquid which is nonmiscible with water. This enables the application of dielectric micromotors which can realize oscillating liquid movements with high efficiency and can deliver well transferable electrical signals (capacity based) for streaming. The application of the nonhydrophilic liquid in the hollow conductor enables the construction of the sensor according to the invention in a simple way and allows for fast diffusional equilibration of the analyte between the whole sensitive polymer phase and the external medium. The surface forces resulting from the contact of the different liquids may be used for prevention of rotating movements of the liquid through the hollow conductor and for restriction of the oscillating movements within a certain amplitude.

Further advantages of the invented principle are the complete independence from the external pressure, as changes in external pressure cannot induce liquid movements in a closed system completely filled with noncompressible liquid, and the potentially small volume of the device, as the sensitive part (dialysis chamber or hollow fiber) has a very small volume.

DETAILED DESCRIPTION OF THE INVENTION

Figure 1:
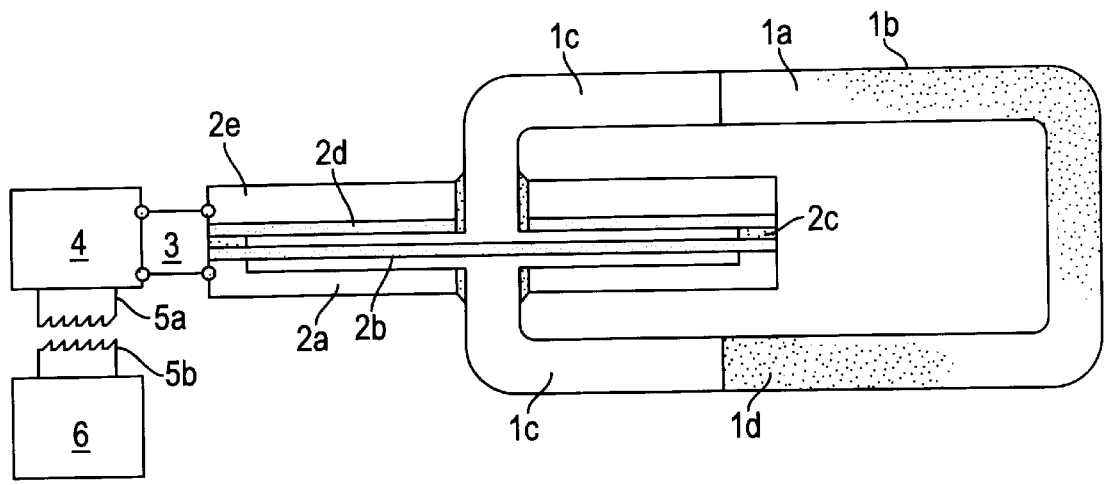
FIG. 1 is a diagrammatic view of a microsensor of a first embodiment of the present invention.
Figure 2:
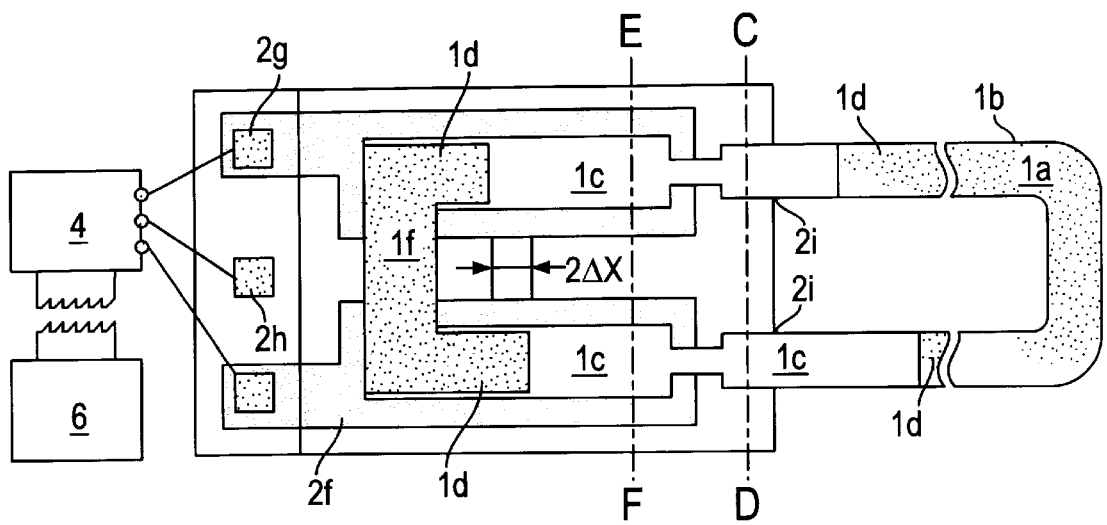
FIG. 2 is a diagrammatic view of a microsensor of a second embodiment of the invention.
Figure 3:
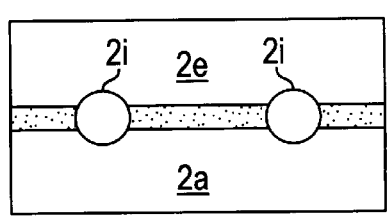
FIG. 3 is a sectional view along line III—III of FIG. 2.
Figure 4:
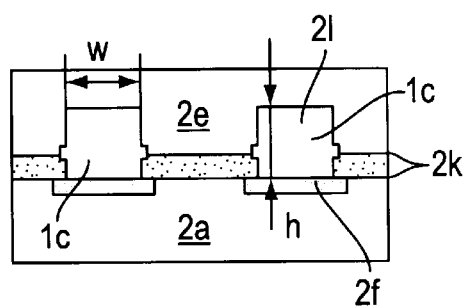
FIG. 4 is a sectional view on line IV—IV of FIG. 2.

FIG. 1 shows a sensor configuration of the first embodiment and FIGS. 2–4 show a sensor of the second embodiment of the present invention.

A dialysis chamber is shown in FIG. 1.

The dialysis chamber consisting of a hollow fiber (1b) filled with a sensitive polymer solution (1a) is connected with an electrostatic micromotor into a hydraulically closed functional unit. The micromotor consists of a metallic (active) membrane (2b), having a first side and a second side a perforated leading membrane support (2a) which is not insulated from the membrane, an insulating ring (2c) which also defines the distance of the membrane to the metallic tap electrodes (2d) and the perforated heading top body (2e). The ends of the hollow fiber (1b) are stuck in the perforations of the membrane support (2a) and of the top body (2e). The inner volume of the micromotor and a part of the bordering hollow fiber are filled with pure silicon oil (1c), which forms stable interfaces (1d) to the analyte-sensitive polymer solution in the hollow fiber and is not miscible with this solution. The first side of the active membrane limits a variable first hollow space (1c) which is connected with one end of the dialysis hollow fiber containing said analyte-sensitive polymer solution. The second side of the active membrane limits a second variable hollow space (1c) which is connected with the other end of the dialysis hollow fiber. The hollow spaces at both sides of the active membrane being separated from the surrounding of the hollow conductor by rigid vacuum tight walls.

The membrane can be moved towards the top electrode by the high electric field in the silicon oil, if a DC or AC voltage is applied between the membrane support (2a) and the top body (2e). The liquid motion in the hollow fiber can be controlled measuring the capacitance between these electrodes as a function of time.

To realize the measuring process in vivo, the membrane support (2a) and the top body (2e) are both connected to a miniaturized transducer unit (4) using a coaxial cable (3). The transducer unit can be wirelessly coupled by means of the coils (5a) and (5b) with the microprocessor-controlled monitoring unit (6) which contains also a power supply. The parts (1)–(4) of the described microsystem, including the first transducer coil (5a), may be completely implanted in the body of the diabetic patient, the hollow fiber being inserted for example into a vein or embedded in the subcutane tissue fluid. The extracorporal part of the microsystem (6) is permanently or temporarily placed on the skin of the patient near to the implanted coil (5a). The implanted part of the microsystem is activated by the energy delivered from the external monitoring unit and does not need an own power supply.

The glucose measurement can be carried out continuously or in adequate time intervals. The described microsystem can also be used to monitor the glucose concentration in a plant organism, a bioreactor or waste water.

In the embodiment of FIGS. 2–4 the micromotor is also used as a sensor for the liquid motion. The micromotor is composed of two thermically bonded Si-chips and. In the top chip (2e) a flat U-shaped deepening is etched forming a flat microchannel between the openings (2i) after the bonding process with the bottom chip (2a). In the bottom chip (2a) two implanted electrodes (2d) are placed symmetrically at the bottom of the U-shaped microchannel, pn-insulated from the substrate and from each other. These electrodes are connected via the bond pads (2g) with a miniaturized capacity measurement set up (4). The capacity of each electrode is measured with respect to the contract (2h) on the chip (2e) consisting of highly dosed silicon. The silicon dioxide layers (2k) with a thickness of about 1 $\mu$m insulate the top chips from the bottom whereas the inside walls at the microchannel are covered by a considerable thinner insulator (thickness about 0.05 $\mu$m). The channel is filled with the liquid (1c), which includes a very small volume of another liquid (1f). The small liquid volume (1f) has a high dielectric constant and/or electric conductance (e.g. water) and is not miscible with the liquid (1c) which is a nonconducting silicon oil with a low dielectric constant, thus forming a stable interface with this liquid. Stable interfaces are also formed between the silicon oil (1c) and the analyte-sensitive polymer solution (1a) in the hollow fiber (1b), connected to the microchannel with the openings (2i). The U-shaped microchannel, and the hollow fiber are completely filled with the liquids (1d), (1), and (1a) without any compressible gas includings. If an HF-voltage source is connected with one of the electrodes (2f), the liquid (1f) will be drawn completely to the corresponding channel region, this way increasing the capacitance between this electrode and the top chip (2e) nearly by the factor $(h/d_{ox}) \times (\epsilon_{ox}/\epsilon_{oil})$. h=height of the microchannel, $d_{ox}$=thickness of the oxid covering the microchannel, $\epsilon_{ox}$, $\epsilon_{oil}$=dielectic constants of oxide and silicon oil.

The pressure driving the liquid (1f) towards the HF-biased electrode can be estimated by calculating the increase of the medium electrical energy stored in the condensator at the applied HV-voltage, if the border area is displaced by a little increment. In our example, the pressure is about 60 mbar at an effective voltage of 30 V. This pressure is sufficient to displace the sensitive liquid (1a) with a velocity linearly dependent on the viscosity of said liquid. If the other electrode is connected with the HF voltage source, the liquids move back and the measuring cycle can start again. For both directions the viscosity can be obtained directly from the capacity change at one of the electrodes.

What is claimed is:

1. A microsensor for the determination of concentration of glucose or other analytes in liquids, based on microsystem technology and viscosity measurement of an analyte-sensitive polymer solution enclosed in a dialysis hollow fiber suitable for implantation in the human body, comprising a hollow conductor; a closed circuit of at least One liquid in said hollow conductor said dialysis hollow fiber containing said analyte-sensitive polymer solution; an analyte concentration measuring system, said hollow conductor combining said dialysis hollow chamber and said analyte-concentration measuring system, said analyte-concentration measuring system including a micromotor for moving said analyte-sensitive polymer solution, said at least one liquid transducing forces between said micromotor and said analyte-sensitive polymer solution within said dialysis hollow fiber, and a Signal transducer operatively connected to said micromotor to generate Signals unequivocally related to viscosity of said analyte-sensitive polymer solutions said signal transducer being selected from the group consisting of a pressure-sensitive signal transducer, a volume-sensitive signal transducer, and a flow-sensitive signal transducer.

2. A microsensor for the determination of concentration of glucose or other analytes in liquids, based on microsystem technology and viscosity measurement of an analyte-sensitive polymer solution enclosed in a dialysis hollow fiber, comprising a hollow conductor; a closed circuit of at least one liquid in said hollow conductor said dialysis hollow fiber containing said analyte-sensitive polymer solution; an analyte concentration measuring system, said hollow conductor combining said dialysis hollow chamber and said analyte-concentration measuring system, said analyte-concentration measuring system including a micromotor for moving said analyte-sensitive polymer solution, said at least one liquid transducing forces between said micromotor and said analyte-sensitive polymer solution within said dialysis hollow fiber, and a signal transducer operatively connected to said micromotor to generate signals unequivocally related to viscosity of said analyte-sensitive polymer solution said signal transducer being selected from the group consisting of a pressure-sensitive signal transducer, a volume-sensitive signal transducer, and a flow-sensitive signal transducer.

3. The micro sensor according to claim 2, wherein said micrometer is identical with said signal transducer by transducing a back-effect of the viscosity—dependent convective resistance of said analyte sensitive polymer solution within said hollow conductor to the movement or energy demand of the micromotor into an electrical signal.

4. The microsensor according to claim 2, wherein said signal transducer includes at least one photosensor which registrates changes in a light intensity around one or more light absorbing or reflecting bodies or interphases between liquids contained in said hollow conductor.

5. The microsensor according to claim 2, wherein said dialysis hollow fiber with the analyte-sensitive polymer solution and said measuring system are co-integrated with a wireless transducing unit for energy and signals forming said signal transducer into a unit which is separated galvanically from an energy source and a display.

6. The microsensor according to claim 2, wherein said hollow conductor contains a liquid which is not miscible with water besides the analyte-sensitive polymer solution, said analyte-sensitive polymer solution and said at least one liquid being not miscible but hydraulically coupled to each other and being mobile withinin said hollow conductor.

7. The microsensor according to claim 6, wherein movement of interfaces between an aqueous phase and a nonaqueous phase is restricted to partial volumes of the hollow conductor according to shape-and material-dependent surface forces between liquids and walls of said hollow conductor.

8. The microsensor according to claim 7, wherein said hollow conductor has one or more parts, where two liquids which are not miscible with each other and differ in dielectrical constant and electrical conductivity touch each other between electrodes of a condensator which is one of said micromotor and said signal transducer.

9. The microsensor according to claim 3, wherein said micromotor and said signal transducer are formed by an active membrane which is hydraulically coupled with said analyte-sensitive polymer solution, for transducing a time-dependent deflection from a rest position between the active membrane and a solid counter electrode into an electrical signal.

10. The microsensor according to claim 9, wherein said counter electrode and a first side of said active membrane limit a variable first hollow space which is connected with one end of said dialysis hollow fiber containing with said analyte sensitive polymer solution, whereas the second side of the active membrane is at the border of a second variable hollow space which is connected with the other end of said dialysis hollow fiber, said first hollow space at the first side of the active membrane and said second hollow space at the second side of the active membrane are separated from surroundings of said hollow conductor and each other by rigid vacuum-tight walls, respectively.

11. The microsensor according to claim 10, wherein a volume of said first hollow space and a volume of said second hollow space are filed with an inert dielectric liquid which is not miscible with said analyte sensitive solution but hydraulically direct coupled to said analyte sensitive solution within said hollow conductor.

12. The microsensor according to claim 2, wherein said dialysis hollow fiber is a dialysis chamber.

* * * * *